US00PP11898P2

(12) United States Plant Patent
Kidwell

(10) Patent No.: US PP11,898 P2
(45) Date of Patent: Jun. 5, 2001

(54) BERMUDAGRASS NAMED '90NB-KID'

(75) Inventor: Jack Kidwell, Boydton, VA (US)

(73) Assignee: Kidwell Organics, Inc., Richmond, VA (US)

( * ) Notice: Subject to any disclaimer, the term of this patent is extended or adjusted under 35 U.S.C. 154(b) by 0 days.

(21) Appl. No.: 09/121,850

(22) Filed: Jul. 24, 1998

(51) Int. Cl.[7] ..... A01H 5/00
(52) U.S. Cl. ..... Plt./389
(58) Field of Search ..... Plt./389

(56) References Cited

U.S. PATENT DOCUMENTS

| | | | |
|---|---|---|---|
| P.P. 7,073 | 12/1989 | Gordon | Plt./389 |
| P.P. 7,081 | 12/1989 | Gordon | Plt./389 |
| P.P. 8,963 | 10/1994 | Vaughn | Plt./389 |
| P.P. 9,888 | 5/1997 | Brown et al. | Plt./389 |
| P.P. 9,976 | 7/1997 | Porter | Plt./389 |
| P.P. 10,079 | 10/1997 | Hanna | Plt./389 |
| P.P. 10,289 | 3/1998 | Krans et al. | Plt./389 |
| P.P. 10,290 | 3/1998 | Krans et al. | Plt./389 |
| P.P. 10,332 | 4/1998 | Krans et al. | Plt./389 |

*Primary Examiner*—Bruce R. Campell
*Assistant Examiner*—Wendy A Baker
(74) *Attorney, Agent, or Firm*—Millen, White, Zelano, & Branigan, P.C.

(57) ABSTRACT

An asexually reproduced variety of bermudagrass with a unique combination of characters including excellent turf performance, aggressive growth, early green up ability, and excellent cold tolerance.

2 Drawing Sheets

BACKGROUND OF THE INVENTION

90NB-Kid is a new and distinctly different variety of bermudagrass (*Cynodon dactylon*) (*SUBFAMILY Eragrostoid, tribe Chloridene). It was discovered near a heavily traveled sidewalk intersection on a college campus adjacent to an athletic field in Annapolis (Anne Arundel County), Md. 90NB-Kid was initially recognized and noted because it had naturalized and was thriving under heavy traffic in the extreme northern part of the transition zone (therefore, the range of bermudagrass adaptability).

A very small initial amount of the 90NB-Kid plant material was asexually propagated at a research and development farm near Baskerville (Mecklenburg County), Va. This was done by cutting stolons and rhizomes, rooting these in soil and planting the rooted cuttings to provide stock for studying performance and for comparisons with existing commercial and experimental varieties of bermudagrass. 90NB-Kid retained both performance and morphological characteristics after this propagation and after repeated repropagation prior to DNA testing.

BRIEF SUMMARY OF THE INVENTION

90NB-Kid is distinguished from other varieties of bermudagrass by the combination of excellent turf performance, particularly in resistance to disease and in recovery from intense traffic and compaction. The plant also exhibits aggressive growth, early green up ability, and excellent cold tolerance.

DESCRIPTION OF THE INVENTION

Figure 1:
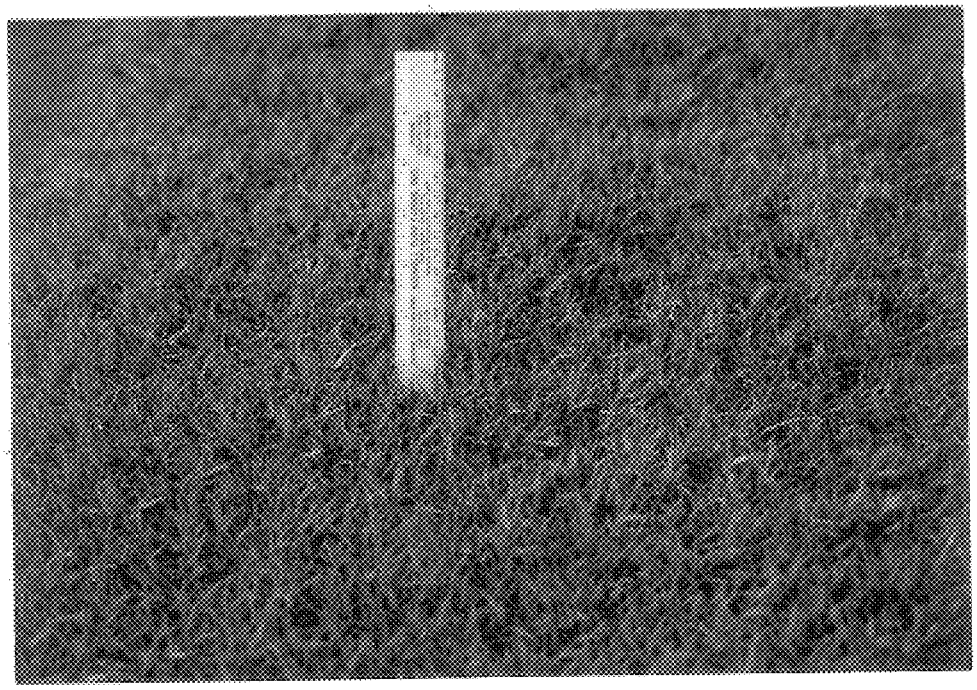
FIG. 1 is a color photograph of a patch of the bermudagrass of the invention at a growth height of about one inch.
Figure 2:
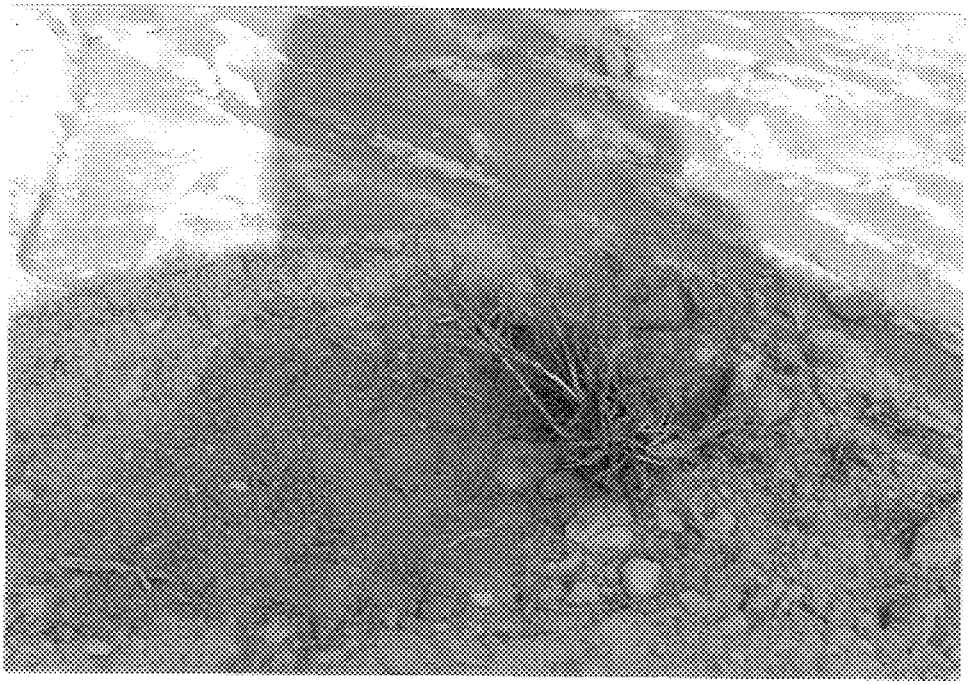
FIG. 2 is a color photograph of the bermudagrass of the invention showing its reproductive parts and some root structure.

90NB-Kid is a new and distinct variety of bermudagrass (*Cynodon dactylon*). The 90NB-Kid variety has been included in the Turfgrass Evaluation Program Trials at the Virginia Polytechnic Institute and State University Turfgrass Research Center in Blacksburg, Va. and at the North Carolina State University Turfgrass Field Laboratory in Raleigh, N.C. where it was favorably rated for winter hardiness, along with other commercial and experimental bermudagrass varieties. In a freeze study, 90NB-Kid was rated in the highest statistical grouping using Duncan's range test, and it was also rated above the Virginia Polytechnic Institute and State University's release, "Vamont", which is considered to be a freeze tolerant bermudagrass.

During extensive observations and studies at the research and development farm at Baskerville, Va., 90NB-Kid has commenced green up seven (7) to ten (10) days earlier than the other commercially propagated bermudagrass on the site. This was regardless of weather conditions and under comparable cultural practices. Typically, this occurs on or about March 25$^{th}$ at this location. However, the early green up did not subject the 90NB-Kid to late freeze damage.

This vigorous northern bermudagrass variety is easily transplanted by stolons or by sod and develops rapidly. Under proper mowing and fertility regimes, coverage from a planting demonstrates that the stolons spread laterally at a rate of 1.8 cm per day, which is also to say that 18 cuttings (sprigs) per square foot reach 90–100 percent ground cover in 45 days. 90 NB reliably produces a commercial sod, that when conventionally lifted is capable of not tearing apart when the strip is supported by ten (10%) percent of its length. It has a pleasing blue-green color, a medium fine texture, is very aggressive in its growth, has excellent resistance to and recovery from intense traffic and compaction, along with excellent cold temperature tolerance. The Turf Research Center, VPI & SU, Blacksburg, Va., conducted freeze studies during 1997 on 90NB-Kid and GN-1 bermudagrass cultivars, using a freeze chamber designed for this purpose. This process is conducted using washed grass materials (no soils), therefore, the temperature readings do not related to ambient temperatures, but rather to actual soil temperatures. GN-1 suffered damage (the ability to regrow normally) at +22 degrees Fahrenheit. When subjected to +18 degrees Fahrenheit, complete loss occurred. 90NB-Kid was subjected to +15 degrees Fahrenheit without injury (somewhat less than "Vamont" bermudagrass), and at +14 degrees Fahrenheit noticeable injury was observed, meaning the threshold for cold hardiness was between +15 degrees and +16 degrees Fahrenheit.

Salt tolerance is good and shade tolerance is average being somewhat better than many other bermudagrass varieties. Over a period of nine (9) years of observation, 90NB-Kid has not been seen to be susceptible to any disease or insect organisms. The fungus "dollar spot" (*Sclerotinia homeocarpa*) has been observed on the plants without causing any pathological symptoms. Under current management practices no significant thatch development has been evident even without clipping removal or cultivation. Overall, this new variety has excellent turf quality characteristics and a high degree of aggressiveness exceeding those of other cold tolerant bermudagrasses. This favorable combination has proven to be ideal for use on athletic fields of all types. To date, 90NB-Kid has been demonstrated on soccer and football fields as far north as Pennsylvania, and as far south as Florida with very favorable results in overall performance and durability.

Figure 3:
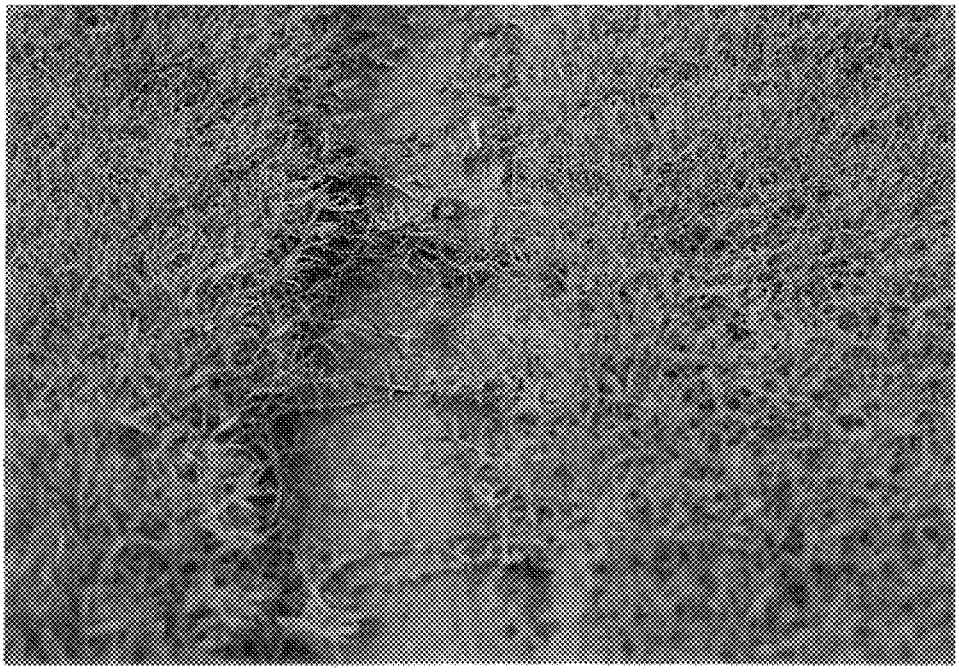
FIG. 3 is a color photograph of the bermudagrass of the invention showing its aggressive growth.

The pleasing bluish-green color and texture can be seen in FIG. 1, and the vigor of the growth can be seen in FIG. 3 where the stolons between two patches of 90NB-Kid bermudagrass represent only ten (10) day's growth. This aggressive growth is remarkable. In a nineteen (19)-day wear-recovery test, the highly regarded Vamont received a high 4.0 rating, while the grass of the invention received an even higher 4.3 rating. Similarly, 90NB-Kid received one of the highest wear tolerance ratings; and, its four (4)-day recovery was even more favorable than Vamont. This, therefore, is a major reason why 90NB-Kid is particularly suited for athletic fields.

Figure 4:
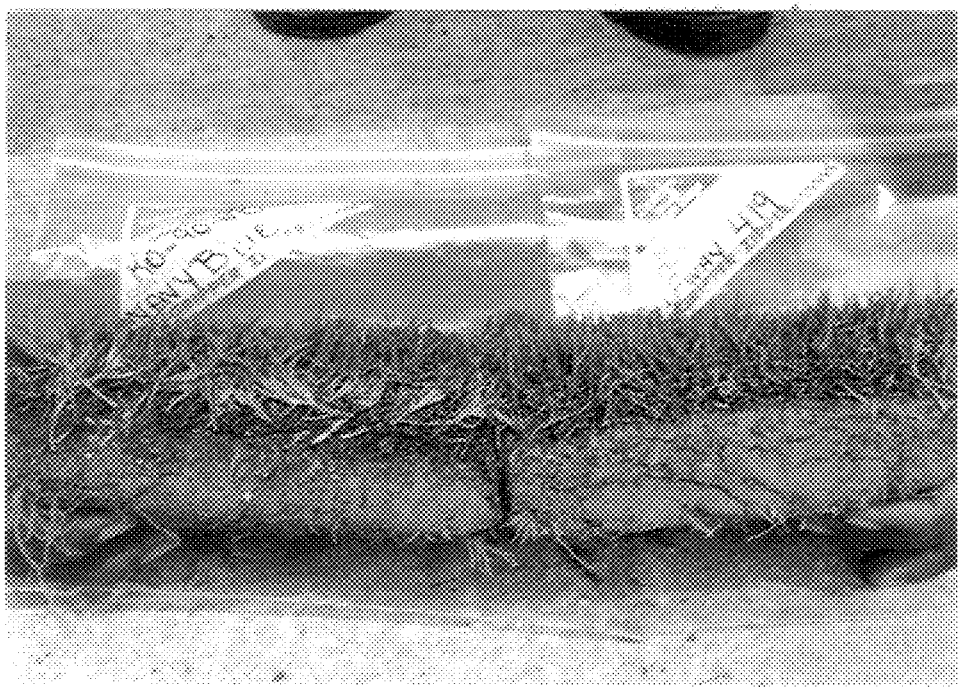
FIG. 4 is a color photograph of a cross section of the bermudagrass of the invention compared to a cross section of Tifway 419.

FIG. 4 shows a comparison between sod pieces of 90NB-Kid and the well-textured Tifway 419. The 90NB-Kid (on the left) is slightly coarser, but the texture of the 90NB-Kid permits it to withstand more traffic, and it recovers from wear almost twice as fast. FIG. 4 shows that 90NB-Kid has deep rhizomes, which may contribute to its cold hardiness. Also, its rhizomes and stolons are shown to be of a robust nature which accounts for its outstanding wear recovery.

DETAILED BOTANICAL DESCRIPTION

Parentage: Unknown (a natural mutation).

Propagation: Vegetative (asexual) by means of planting chopped stolons and rhizomes.

Growth habit: A low-growing warm season stoloniferous rhizomatous perennial grass forming a dense sod. Rhizomes are found at a depth of greater than 5 cm., allowing rapid regrowth and recovery from thick sod harvesting (3.75–4 cm.). Stolons and rhizomes branch from the nodes.

*Average node diameter*.—1.6 mm.

*Average internode diameter*.—1.0 mm.

*Average internode length*.—1.8 cm.

Leaf blade: Glabrous, folded in the bud shoot, 2.2–3.5 cm in length, 1.75–2.1 mm in width with parallel venation visible under low magnification (10×), tapers toward the tip to an acute point. Slightly variable with fertility and micro-fertility regimes.

Sheath: Open, shorter than the internode.

Ligule: A whitish fringe of hairs 1mm in length.

Collar: Narrow and continuous, constricted at the mid vein.

Auricle: Absent.

Inflorescence: Sparsely produced; not produced at typical athletic turf mowing heights of 1.25–3.75 cm. When produced, 4 to 5 digitate spikelets bearing seeds found to be of very low number and viability such as to be incompatible with commercial sod production.

Unmowed height: 15 cm.

Colors of Plant Parts as Compared to the Pantone ® Book of Color, L. Eiseman & L. Herbert, Harry N. Abrams, Inc. Publishers, NY, NY @ 1990:

| Area of 90NB-Kid | Pantone Color | Description |
|---|---|---|
| Leaf Surface | Chive | |
| Leaf underside | Black Forest | |
| Rhizome | Brown | |
| Stolon Sheath | Grasshopper striated with Pale Star | |
| Culm | Peridot | |
| Spikelet | Chive | 3 each 21 mm long, 10 mm diameter, total seed head 50 mm tall |
| Ligule | Frozen Dew | Fringe of hairs |
| Collar | Frozen Dew | Narrow band restricted centrally |
| Anthers | Dawn Pink | |
| Stigmas | Black Forest | |
| Lemmas | Cidrada | |
| Node | Moth | |
| Internode | Murmur | |

Rooting: As 90NB-Kid is vegatively propagated the roots arise from nodes of both stolons and rhizomes (nodal or adventitious roots), which are in the ground contact. Thus, the entire root system can be characterized as adventitious roots that develop further along laterally and tend to become rudimentary unless the stolon or rhizome is severed. In this case the rudimentary roots rapidly develop to support the severed portion of the plant. This is the reason that the variety is so easily vegetatively reproduced.

What is claimed:

1. A new and distinct variety of bermudagrass plant, substantially as herein shown and described, characterized particularly as to novelty by excellent turf performance, especially traffic and compaction resistance and recovery, excellent color and turf density, aggressive growth, early green up ability, and excellent cold tolerance.

* * * * *